United States Patent
Winsel et al.

[11] Patent Number: 6,103,075
[45] Date of Patent: *Aug. 15, 2000

[54] LINEAR ELECTROCHEMICAL CONDUCTOR ELEMENT

[76] Inventors: August Winsel, Fasenenstrasse 8A, D-65779 Kelkheim; Hans Sauer, Pflasterwiese 7, 65510 Idstein-Walsdorf, both of Germany

[*] Notice: This patent is subject to a terminal disclaimer.

[21] Appl. No.: 09/179,004

[22] Filed: Oct. 26, 1998

Related U.S. Application Data

[63] Continuation-in-part of application No. 09/088,992, Jun. 2, 1998, Pat. No. 6,045,938.

[51] Int. Cl.[7] ............................................. C25B 11/00
[52] U.S. Cl. .................. 204/280; 204/279; 204/282; 204/252; 204/265; 429/59; 429/225
[58] Field of Search .................... 204/279, 280, 204/265, 252, 282; 429/59, 225

[56] References Cited

U.S. PATENT DOCUMENTS 5,242,565  9/1993  Winsel ..................... 204/265
5,407,555  4/1995  Winsel ..................... 204/433

*Primary Examiner*—Bruce F. Bell
*Attorney, Agent, or Firm*—Schnader Harrison Segal & Lewis LLP

[57] ABSTRACT

The invention pertains to linear electrochemical functional elements which have strip-shaped ion-exchange membranes (IEMs) and/or hydrogen-diffusion electrodes accessible at the ends which are enclosed on all sides in an insulating manner by a jacket of a solid material. The invention describes the structure, production, and use of the functional elements in electrochemical measuring techniques. In one embodiment, a charge state indicator is created by the incorporation of a lead/lead sulfate half-cell into a lead/lead oxide cell. This coupling takes place via a linear functional element in the form of an installed ion-exchanger membrane. It makes it possible to measure three voltage values on the cell and to evaluate them in order to determine the current charge state by conventional methods.

13 Claims, 6 Drawing Sheets

Cut
A-A

LINEAR ELECTROCHEMICAL CONDUCTOR ELEMENT

CROSS-REFERENCE TO RELATED APPLICATIONS

This is a continuation-in-part of U.S. application Ser. No. 09/088,992, filed on Jun. 2, 1998, now U.S. Pat. No. 6,045,938.

BACKGROUND OF THE INVENTION

1. Field of the Invention

The present invention relates linear electrochemical functional elements, processes for their production, and measuring instruments using them.

2. Description of the Related Art

The primary field of application of the linear electrochemical functional element described in the following is electrochemical measurement techniques, especially with hydrogen electrodes. From German patent DE-PS 41 12 784.6 and the corresponding international application PCT/EP 92/00597, a hydrogen rod electrode with integrated hydrogen source is known. In it, a hydrogen evolution cell according to German patent DE-PS 35 32 335 is used in order to supply a hydrogen-diffusion electrode with hydrogen. Two constructions are described there which differ with respect to the active measuring electrode. The essential elements of the design are described in FIGS. 1 and 2.

In FIG. 1, the hydrogen electrode 101 is a platinized platinum wire which is positioned in the opening of a hydrogen tube 103 tapering to a point and made of glass, Plexiglas, or other material that is as impermeable to hydrogen as possible. The other end of the hydrogen tube is screwed, plugged, or glued gas-tight into the actual gas cell container 107. This preferably cylindrical gas cell container 107 holds the hydrogen evolution cell 109 according to German patent DE-PS 35 32 335. It contains zinc powder or zinc gel and caustic potash together with the so-called hydrogen evolution electrode. On the latter, a PTFE-bound catalyst film is rolled into a metal net and carries, on the side away from the zinc, a laminated-on fine-pored PTFE foil. The zinc electrode and the hydrogen evolution electrode are located in a housing which is usually made up of two metal parts insulated from each other, one of which is connected to the zinc electrode, the other to the hydrogen evolution electrode in an electron-conducting manner. The housing part containing the hydrogen evolution electrode communicates via at least one boring with the interior of the gas tube 103. The boring can be sealed by a sticker which releases the hole during operation of the cell as a result of excess pressure. The sticker may be a metal foil such as copper according to German patent application DE 195 07 658.3.

The gas cell container 107 is closed by the screwed-on or pushed-on lid 110, which may have several functions. Thus, after the closing, advisably by means of elastic spring elements (not shown), it exerts a pressure on the cell 109 so that the latter communicates by means of the ring-shaped gasket 108 through the aforementioned boring in the cell housing part with the gas tube 103. These spring elements may be the electronic contacts 112 and 113, which contact the two housing parts. The lid 110 also advisably carries a fixed or variable electrical resistance 111 in series with an on-off switch to which the contacts 112 and 113 are connected. This may be, for example, a potentiometer with an "off" position.

Instead of a lid, this electrical switching and current-regulating circuit may also be connected to the gas cell container 107.

To avoid disturbances caused by foreign gases, the metal layer from the hydrogen electrode is guided, inside the hydrogen tube if possible or embedded in its jacket, to the gas cell container where it terminates in a contact screw 106 accessible from the outside or a single-pole plug socket.

Platinum electrodes are suitable especially for use in acid media, because they resist all oxidizing acids in them. In addition, however, many other metals of the 8th Group of the Periodic Table of Elements, their alloys, or electron-conducting solid bodies metallized with them are suitable for use as long as they possess the catalytic capabilities for chemisorptive splitting of the hydrogen molecule. This is true, for example, for palladium and iridium, but also for activated carbon which is catalyzed by these metals. In this case, black, large-area coatings are characterized as especially effective. In alkaline and neutral solutions, nickel is a highly effective hydrogen catalyst, especially in the form of Raney nickel. This is a powdered material that is obtained from a nickel/aluminum alloy by extraction of the aluminum with a caustic alkali. Hydrogen electrode bodies can be produced from it by means of powder-metallurgical production processes. Such procedures are described in the book *Fuel Cells* by E. Justi and A. Winsel, Steiner Verlag, Wiesbaden 1962 and the patents listed in it. Electrodes suitable for this purpose, however, are also produced from a catalyst powder by intensive mixing with PTFE powder in a very high speed knife mill and rolling the powder mixture out into a metal net. Such electrodes are also advisably coated on one side with a fine-pored hydrophobic PTFE film that faces the reacting gas and keeps the three-phase boundary electrode/electrolyte/gas stable. Such electrode structures are described in European patent EP-PS 144 002 (1983). However, it may be advantageous to improve the storage capacity by using so-called hydride storage alloys in addition to the Raney nickel, as described in German patent DE-OS 37 02 138 (1987).

In FIG. 2, the hydrogen electrode 101 is such a gas diffusion electrode which is contacted with a metal ring 102 and which is affixed by the holding cap 104 to the tube 103. It may be used in any position in an electrochemical measuring cell. The coupling of the above-described hydrogen electrode with the measurement object in an electrochemical cell is determined by the geometric shape and the inflexible structure. However, it is desired to have a reference electrode which can be installed as closely as possible to the contact of an equipotential surface also in a narrowly constructed primary or battery cell.

In a polyelectrolyte (PE), one type of ion is macromolecular and polyvalent, while the counterion consists of the usual highly mobile ions. Both types of ions are hydrated and participate in water exchange in osmotic competition with their surroundings. In ion exchangers (IEs), many such macromolecular ions are connected by covalent bonds to networks that are insoluble because of their size. Therefore, they consist of fixed ions and mobile counterions which dissociate away according to the law of mass action and which can be replaced by ions of the same sign. Only these mobile counterions may contribute to electrical transport; the non-mobile fixed ions do not contribute to the conductivity. There are anion exchangers (AIEs) with mobile anions as counterions and a polyvalent cationic solid, as well as cation exchangers (CIEs) with mobile cations as counterions and a polyvalent anionic solid. Ion-exchange membranes (IEMs) are homogeneously or nonhomogeneously constructed membrane bodies which, because of their exchange action, involve only the counterions in the mass transfer by electric current and electro dialysis.

Generally, the ion exchanger excludes the penetration of ions of the same sign as that of the solid ions. In the case when ion exchangers and ion-exchange membranes are used in highly concentrated solutions, especially strong electrolytes, foreign ions of the same sign as the solid ions are carried into the solid body with the water of hydration, thereby contributing to the electrical current and electrodialytic mass transfer. However, even in such small three-dimensional elements of IEs and IEMs, the charge balance is always neutral when averaged over time. For extensive literature on IEs and IEMs refer to "Rompp Chemie Lexikon", vol. 3, published by Jurgen Falbe, Manfred Regitz (1995), Verlag G. Thieme, Stuttgart, Germany.

The swelling behavior of IEs and IEMs is determined by the water economy. It can be used to measure the concentration in aqueous solutions. A simple representation of the processes occurring here is given in the following article: A. Winsel "Concentration measurements with ion-exchange membranes," Chemie-Ing.-Techn. 44 (1972) 163–167.

If one conceives of an IE or an IEM enclosed in a solid and non-deformable housing with walls that are permeable for water vapor but are impermeable for non-water molecules, then a hydrostatic pressure gradient is formed between the inner and outer space. This is equal to the osmotic pressure difference between the IE or IEM, on the one hand, and the surrounding solution, on the other. If the osmotic pressure gradient is always directed in such a way that the enclosed IE can remove water from the environment, then the E cannot change significantly in its ion concentration nor in its water content and other characteristics.

A large number of ion exchangers and ion-exchange membranes exists. Thus the polyvalent solid may be a strong acid radical $[-SO_3-]_n$ or a weak acid radical $[-COO^-]_n$, but it may also be a strong $[-N(CH_3)^+]_n$ or weak base $[-N(CH_2)^+]_n$. In each case, neutralized with the corresponding counterions, there are a large number of salts. They may dissociate according to the mass action laws valid in each case and conduct electric current. In suitable combination, they are buffering substances that adjust a narrow pH value. In electrochemistry in recent decades, the membrane invented by W. Grot and made of NAFION®, a poly(perfluoroalkylene)sulfonic acid, has proven especially effective. NAFION® is a trademark of the Du Pont Co. The NAFION® material is available as a powder or as a solution. Ion-exchange membranes of NAFION® material are freely supporting or welded onto PTFE fabric. Membrane-like ion exchangers can be produced in various ways. This is especially simple if the powdered initial material of an IE is mixed with PTFE powder in a high-speed knife mill (reactive mixing) and a skin is formed from the cotton-like material by rolling. This IEM skin in a broad range of compositions consists of a cohesive cold-welded ion-exchange skeleton in a netlike PTFE web. An electrolytic conducting structure is formed both with and without secondary thermal treatment within the IEM body despite the hydrophobic action of the PTFE as a result of swelling. By mixing in powdered buffering salts, one can assure that the ion concentration as well as the pH will vary only slightly with the IEM in the application case.

By mixing in catalyst powders for the hydrogen reaction, biporous structures can be produced in which the IE skeleton forms the electrolyte and the catalyst skeleton the electron conductor. The gas in question may flow in the hydrophobic range of the PTFE structure. As catalyst powder, activated carbon especially is used alone or as a carrier for the mobile metal catalyst of platinum, palladium, nickel, or other metals or alloys. However, metallic catalysts may also be used as highly coarse powders such as the Raney metals. These are obtained as residual metals by dissolving an alloying component out of a powdered alloy.

SUMMARY OF THE INVENTION

The invention pertains to linear electrochemical functional elements which have strip-shaped ion-exchange membranes (IEMs) and/or hydrogen-diffusion electrodes accessible at the ends which are enclosed on all sides in an insulating manner by a jacket of a solid material. The invention describes the structure, production, and use of the functional elements in electrochemical measuring techniques. In one embodiment, a charge state indicator is created by the incorporation of a lead/lead sulfate half-cell into a lead/lead oxide cell. This coupling takes place via a linear functional element in the form of an installed ion-exchanger membrane. It makes it possible to measure three voltage values on the cell and to evaluate them in order to determine the current charge state by conventional methods.

In one embodiment, the present invention is a linear electrochemical functional element, comprising a strip-shaped half-cell accessible at both ends and enclosed by a jacket of a solid insulating material.

In another embodiment, the present invention is an electrochemical cell for measuring pH and/or concentration of a solution in an electrochemical object, comprising (a) an electrode being a half-cell, and (b) a reference hydrogen rod electrode with integrated hydrogen source, wherein a linear electrochemical functional element connects the hydrogen rod electrode to an electrolyte of the electrochemical object to function as an electrochemical key and the voltage between an electrode of the electrochemical object and the hydrogen rod electrode is measurable.

In yet another embodiment, the present invention is a charge state indicator for lead battery cells with a linear electrochemical functional element comprising a strip-shaped ion-exchange membrane (IEM) accessible at an end and which is enclosed in an insulating manner by a jacket of solid material wherein a first end of the functional element is immersed in an electrolyte of a battery cell while a second end opens in the electrolyte of a half-cell to function as an electrochemical key, the half-cell having components of a lead electrode and comprising a lead grating as a lead-off conductor, a negative porous mass, and sulfuric acid as an electrolyte and wherein the voltage between the lead-off conductor of the half-cell and one of the electrodes of the battery cell corresponds to a state of charge of the battery cell.

In still another embodiment, the present invention is a method for manufacturing a half-cell for use in a charge state indicator, comprising the steps of (a) preparing a cup-shaped vessel of a metal stable in sulfuric acid at the potential of a lead/lead sulfate electrode; (b) introducing negative mass in the form of a paste of tribasic or tetrabasic lead sulfate and sulfuric acid; (c) transforming the paste into lead sponge by electrochemical reduction in sulfuric acid by wiring the vessel as the negative pole in a formation cell; (d) introducing a linear functional element as a electrochemical key into the vessel; and (e) deforming the vessel until it fits closely around the linear functional element.

In still yet another embodiment, the present invention is a method for using a charge state indicator for regulating the charge of a battery cell, comprising the steps of (a) determining a voltage $U_{1,2}$ between a negative pole and a positive pole of the battery cell; (b) determining a voltage $U_{1,3}$ between the negative pole and a half-cell of the battery cell; (c) determining a voltage $U_{2,3}$ between the positive pole and the half-cell; (d) charging the battery with a high charging current until the voltage $U_{1,3}$ reaches a voltage plateau $(U_{1,3})_{gas}$ corresponding to the beginning of hydrogen evolution at the negative pole and then lowering the charging current to a preset value; and (e) switching off the charging current or lowering the charging current to a value near a self-discharge current of the battery cell, when the voltage $U_{2,3}$ reaches a voltage value $(U_{2,3})_{gas}$ corresponding to the beginning of gas evolution at the positive pole.

BRIEF DESCRIPTION OF THE DRAWINGS

Other aspects, features, and advantages of the present invention will become more fully apparent from the following detailed description, the appended claims, and the accompanying drawings in which:

DETAILED DESCRIPTION

Figure 1:
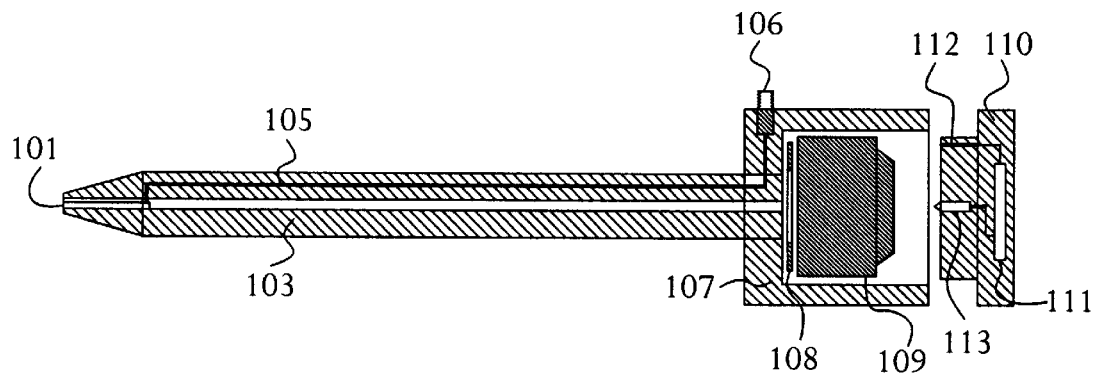
FIGS. 1 and 2 show cross-sectional views of conventional gas diffusion electrode.

It is possible to produce useful linear conducting structures from gas electrodes that are both stable in shape and stable in potential. For this purpose, a strip is cut out of an electrode tape, placed in the fitting grove of a casting die, and embedded in casting resin on all sides. In this way, an electronically conducting, catalytically acting, electrolyte drawing strip of, e.g., 2-mm width and 1-mm thickness, which is open at both ends is formed. On one side, it can be supplied with hydrogen and electrically contacted, while, on the other side, it can be immersed in the electrolyte of the measuring cell. The strip is flexible and may be used, for example, in the set of plates of a starter battery or in a fuel cell as a reference electrode. Thus, the polarization behavior of the two electrodes can be monitored during a load on the measuring cell.

In order to obtain an especially stable linear structure, the electrode strip can also be inserted in a flat metal tube that has a passive surface at the potential of the gas electrode. This is the case, for example, for hydrogen electrodes in the presence of copper and nickel and all noble metals. Titanium which becomes coated with a nonconducting and insoluble film of $TiO_2$ may also be used. Anodized aluminum also has this property of being passive to many solutions. In order here also to exclude reactions on the outer surface of the tube, it may be coated with an insulating enamel or resin. For this, one may also use polymer heat-shrinkable tubing of polyethylene, polyvinyl chloride, or polyvinyl fluoride, for example. See Encyclopedia of Polymer Science and Engineering vol. 7, p. 81 et seq. In many cases, it is advantageous to place the electrode strip directly in the heat-shrinkable tubing and to shrink it in a stream of hot air or under a flatiron or in a hot roll in order to produce a linear gas electrode with an insulating coating.

For the version of a linear electrode strip described above, practically all structures of gas electrodes are suitable. They may consist only of a rolled skin. For this purpose, catalyst powder and PTFE powder are mixed reactively and shaped in a roll. In addition, however, the electrode may also contain a metal net which improves the electrical conductivity in the direction of the strip. It may also contain a laminated-on PTFE foil in order to facilitate the longitudinal flow of the reaction gas. Of interest for the applications to be described in detail below are those linear structures in which IEM strips and gas electrode strips form a half-cell by overlapping. It is advantageous if the overlap zone is tightly welded by pressing or hot pressing. The hydrogen electrode then operates in an IE electrolyte which is specified by the nature and concentration of the ion exchanger and may be used as a standard.

The individual linear functional elements and their coupling to the hydrogen rod electrode with an integrated hydrogen source will now be described in some examples. For simplicity, in the examples, the other part of the gas tube together with the container will be regarded as a constant component for the gas evolution cell.

Figure 2:
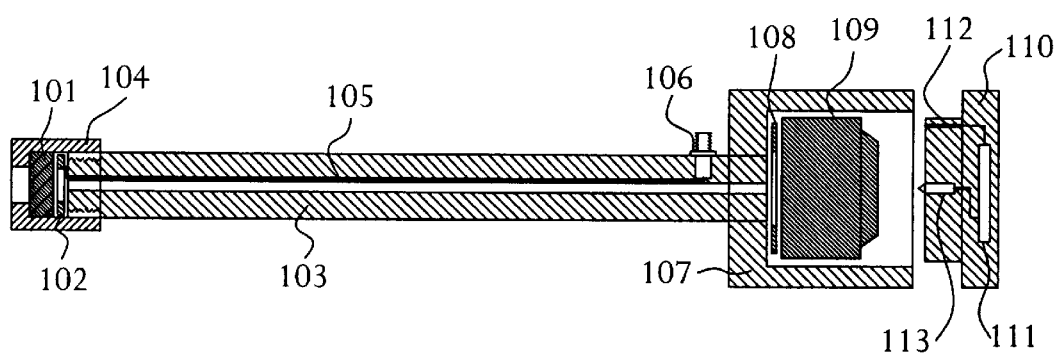
Figure 3:
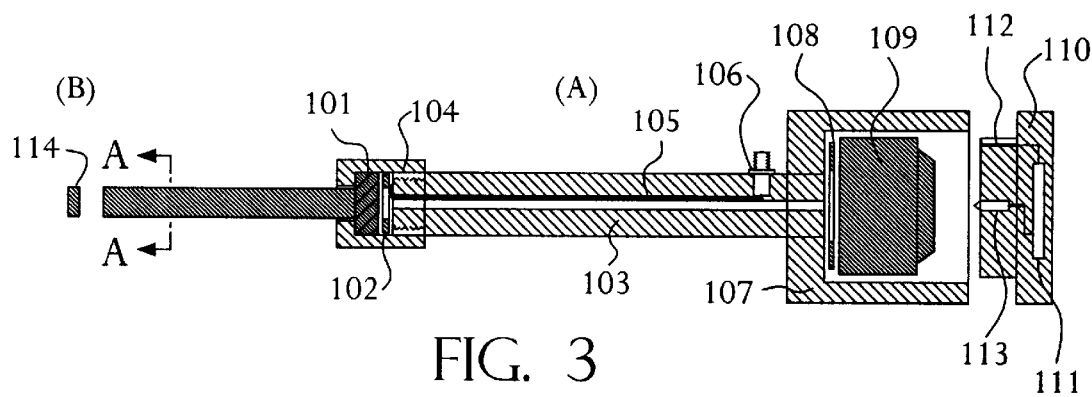
FIGS. 3A–B show cross-sectional side and end views of a gas diffusion electrode with a tongue-like tip, according to one embodiment of the present invention.

FIGS. 3A–B shows how the hydrogen rod electrode shown in FIG. 2 can be provided with a tongue-like tip 114. FIG. 3B, which is section A—A of FIG. 3A, illustrates the strip-like character of the linear IEM element. It is inserted or glued in a closely fitting manner into the holding cap 104 and contacted electrolytically with the hydrogen electrode 101. The front end of the tongue scans the electrode potential in the measuring cell.

Figure 4:
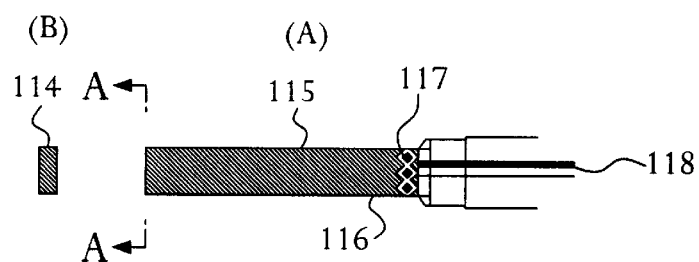
FIGS. 4A–B show cross-sectional side and end views of the linear functional element of a gas diffusion electrode of the present invention.

In FIGS. 4A–B, the linear functional element consists of a linear half-cell which is formed from an IEM strip 116 and an electrical chemically connected electrode strip 117. Both are embedded in a casting resin and are plugged onto the hydrogen tube with heat-shrinkable tubing 115. Element 118 illustrates the "broken" hydrogen tube with contact wire which conducts the electrode potential to the measurement terminal.

During production, the heat-shrinkable tubing is pulled onto the tube end coated with epoxy resin, and the linear half-cell element also coated with epoxy resin is inserted. The tubing is shrunk in a hot-air blower and the resin is simultaneously cured. By this elegant method, numerous combinations of IEMs and electrodes can be produced as linear functional elements and mounted on electrochemical measuring devices with screw or plug adapters.

Figure 5:
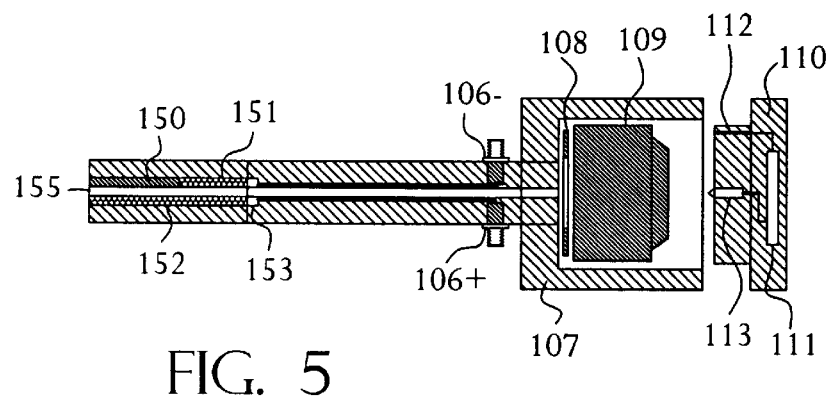
FIG. 5 shows a cross-sectional view of a gas diffusion electrode, according to an alternative embodiment of the present invention.

In FIG. 5, a new type of device is shown which can be realized with the aid of the linear functional elements described here. It has three linear electrochemical elements 150, 151, and 152 in a hydrogen tube. The IEM 150 forms with the hydrogen electrode 151 a linear half-cell which is supplied with hydrogen in the space 153 from the gas evolution device. From the space 153, the hydrogen electrode 152 also gets its gas, hydrogen electrode 151 is connected to the contact screw 106+, and hydrogen electrode 152 with the contact screw 106−. Upon immersion of the tip of the device 155 into an electrolyte solution, one measures on the terminals 106+ and 106− a voltage reflecting the pH of the solution relative to that of the IEM 150. If a current is flowing in the measurement electrolyte then in front of 155, additionally a potential gradient prevails which is superimposed on the measurement. The component of this field which is present parallel to the end face 155 and which delivers a corresponding contribution to the voltage (106+, 106−) reverses this voltage contribution upon rotation of the device by 180°. In this way, the fraction of impressed and reactive voltage in (106+, 106−) may be identified.

The common supply of the two hydrogen electrodes from one source eliminates the effects of hydrogen pressure and hydrogen temperature which are the same for both. In a gas tube, instead of the one half-cell combination (150, 151), there may be many of them, which are characterized by different IEMs, i.e., by different pH values. The corresponding linear functional elements may be arranged in the manner of a turret around a hydrogen electrode. They may open at the height of the terminals 106+ and 106− in a circle of contacts on which a voltage can be measured in each case in pairs. As a result, the possibility also exists of adaptation of the measurement standard to the pH of the object solution.

As just described, a device according to the invention may have two or more halve cells. Each of these halve cells comprises a strip made of a gas diffusion electrode material on the top that is constructed as described earlier. It may be advantageous, if one of these halve cells is not connected to the hydrogen supply, but rather open to the access of oxygen from the air. In this case, the air-connected halve cell forms a fuel cell with a similar constructed hydrogen-supplied halve cell. Its theoretical voltage is 1.23 V. Due to the uncertain oxygen potential, this voltage reduces to about 0.8 V to 1.1 V in practice. This construction allows control of the proper function of the hydrogen supply and of the hydrogen electrodes. If the "fuel cell voltage" drops down below 0.5 V, the device needs maintenance.

Figure 9A:
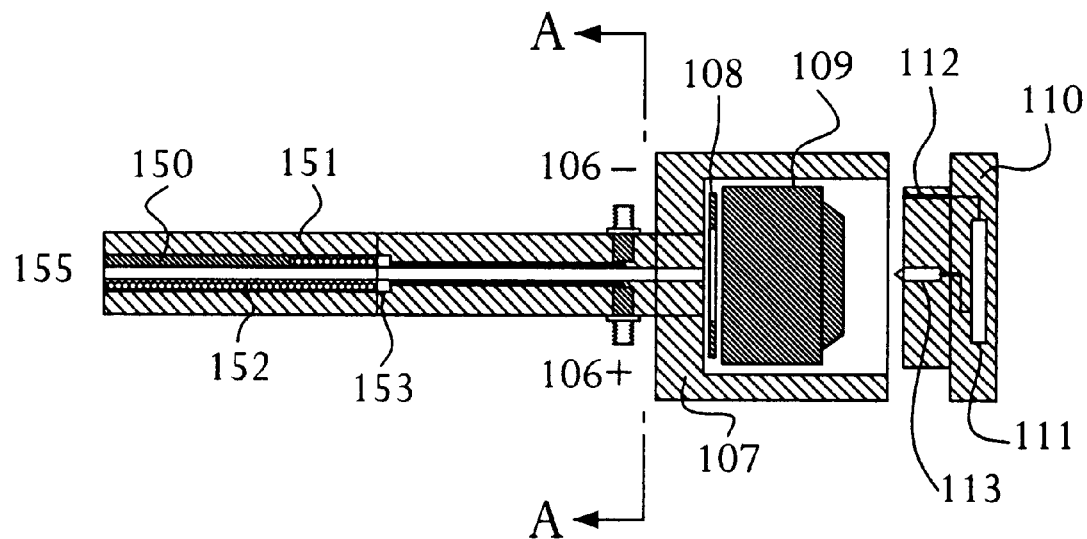
FIGS. 9A–B shows cross-sectional side and end views of an embodiment of the present invention having four linear elements, one of which is configured to the air, rather than to a hydrogen supply.
Figure 9B:
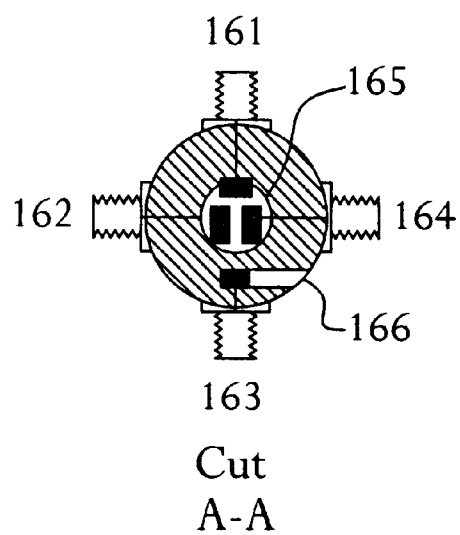

FIGS. 9A–B shows cross-sectional side and end views of an embodiment of the present invention having four linear elements, one of which is configured to the air, rather than to a hydrogen supply. Each of the four linear elements is connected to one of the electronic contacts 161–164. Three of the four linear elements are connected to the hydrogen supply bore 165, while drill hole 166 connects the fourth linear element to air to allow the access of oxygen to this element.

The dimensions of the linear elements which are stated above at 2-mm width, 1.5-mm thickness and any length, correspond to the frequently desired technical requirements. However, they also correspond to the adaptation to simple measuring instruments with conventional internal resistance. Interesting applications, however, arise through miniaturization in the case of medical applications since a regulated hydrogen source is also smaller than or may also be smaller than a swallowable tablet. The linear functional elements described here recognize no lower size limits.

The invention finds a simple application in determining and indicating the state of charge in lead batteries. Since the sulfuric acid of a battery cell is a part of the active mass and is bound as lead sulfate upon discharging, its concentration very precisely reports the charge that can still be drawn. In modern battery engineering, however, use is increasingly being made of systems in which the electrolyte is present in the form of a gel or in fleece-like separators. Then the acid accessible outside of the set of plates correlates only poorly with the actual state of charge. This invention of the linear functional elements enables one to insert one end into the set of plates between a positive $PbO_2$ electrode and a negative Pb electrode. This may be both the IEM strip as well as a hydrogen-diffusion electrode strip. In the case of the IEM strip, the latter may, as an electrochemical key, form the connection with any reference electrode, preferably a hydrogen rod electrode as in FIGS. 3A–B. In the case of the hydrogen electrode, the arrangement shown in FIGS. 4A–B has proven effective. The voltage between the negative lead electrode of the battery cell and the reference electrode may be read out directly in units of the quantity of charge still available with consideration of the construction data of the battery cell.

As described above, useful linear conducting structures can be made from ion-exchanger membranes (IEM) which are both shape stable and also stable in pH. For this purpose, a strip of an IEM is cut out, placed in the fitting groove of a casting tool, and embedded on all sides in a casting resin. Thus, an electrolytic conductor of, e.g., 2-mm width and 1-mm thickness, is formed which is open at both ends and which can be used as an electrolyte key for electrochemical measurements. It is flexible and, for example, can be used in the set of plates of a starter battery. As a connection to a reference electrode (electrochemical key), in this way, the polarization behavior of the two electrodes of the battery cell can be monitored exactly during the charging and discharging of the cell by measuring.

In order to obtain an especially stable linear conductor, the IEM strip can also be introduced into a round or flat metal pipe which has a passive surface. This is the case, e.g., with titanium, because titanium becomes coated with a nonconducting and insoluble film of $TiO_2$. Anodized aluminum also has the property of being passive to many solutions. In order to exclude reactions on the outer surface of the pipe, it can be given an insulating coating with an enamel or resin. For this purpose, one can also use a polymer shrink-fit hose of polyethylene or polyvinyl chloride which may also have a film of cast resin in the inside.

In many cases, it is advantageous to insert the IEM strip with or without the casting resin directly into a shrink-fit hose and shrink it in a stream of hot air, at which time, the casting resin also is cured. The heating can also take place under a hot flat iron or in a hot roller in order to produce a linear ionic conductor with insulating jacket.

The above-stated idea can be modified for the construction of a charge state indicator for lead batteries. It has been found that, contrary to expectations, the acid IEM is not rapidly neutralized by the lead ions of the lead battery, which would make it useless, but rather remains capable of being used sufficiently long for economical use. On the basis of this discovery a charge state indicator has been developed as described with reference to FIGS. 6 through 8.

Figure 6:
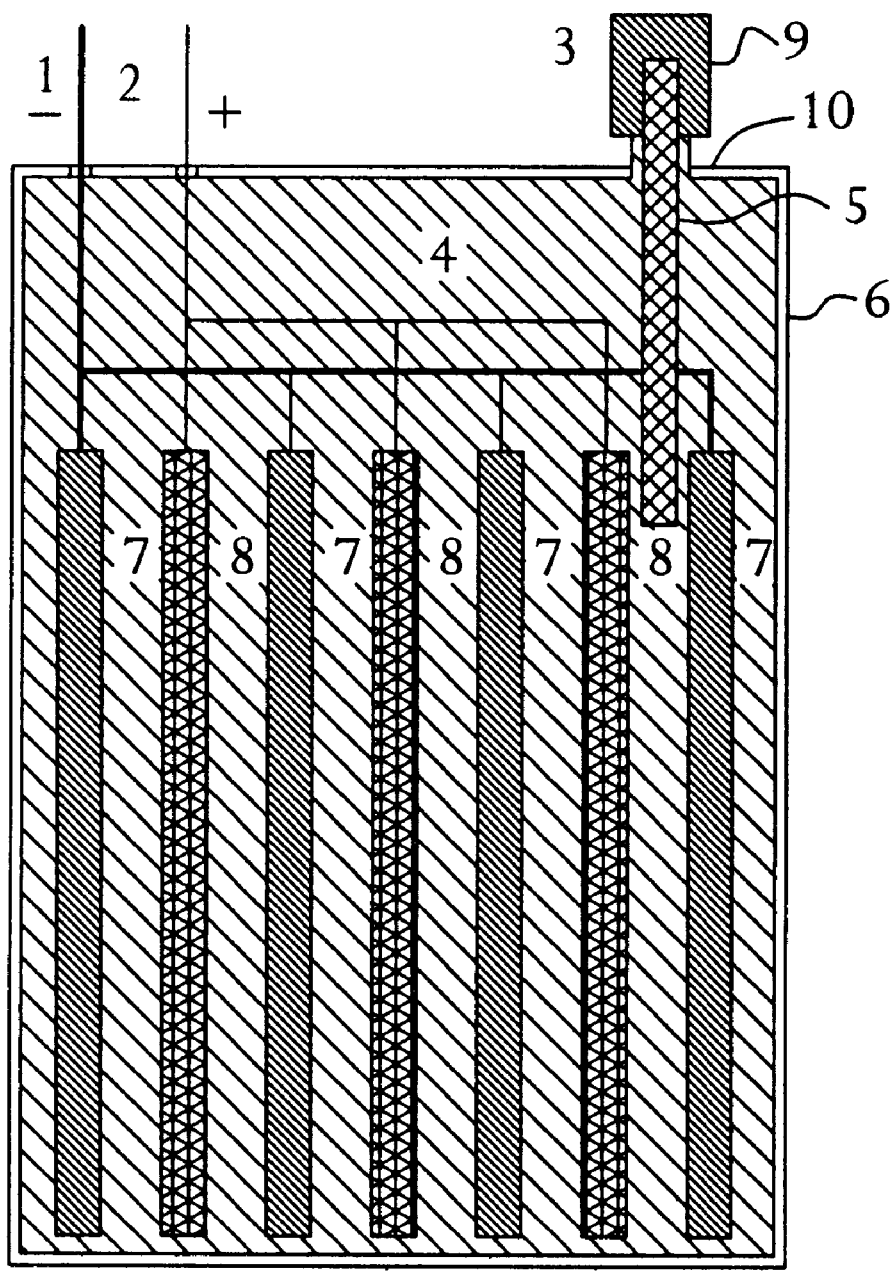
FIG. 6 shows a schematic diagram of a lead battery, according to one embodiment of the present invention.

FIG. 6 shows schematically but very realistically the cell of a lead battery. In the housing 6, it contains four negative lead electrodes 7 which are connected by a pole bridge to the negative terminal 1. It also contains three positive electrodes of $PbO_2$ 8 connected to the positive terminal 2 in the sulfuric acid 4. The sulfuric acid may optionally be liquid or immobilized in a silica gel. As in every lead battery, the cell also contains separators between the individual electrodes which are not indicated for the sake of better clarity. Whether formed with a microporous structure or as fleece, each separator influences the acid economy of the individual electrodes by its electrolyte displacement and by its diffusion and migration resistance. However, this fact plays only a subordinate role for this invention. In FIG. 6, the charge state registration is made possible by the half-cell 3 which is immersed with the linear functional element 5 as an electrochemical key in the electrolyte 4 of the cell. The useful information on the current charge state is obtained when the electrochemical key ends between a positive and a negative electrode. An advantageous position, however, is also the center of the plate on one of the end plates outside of the set of plates. The half-cells 3 comprise a hollow metal body 9 as a lead-off conductor and, in the inner space, a highly porous lead sponge and sulfuric acid, the components of a negative lead electrode. On the through-guide 10, the unit of linear functional element and half-cell is firmly connected to the battery housing.

Figure 7:
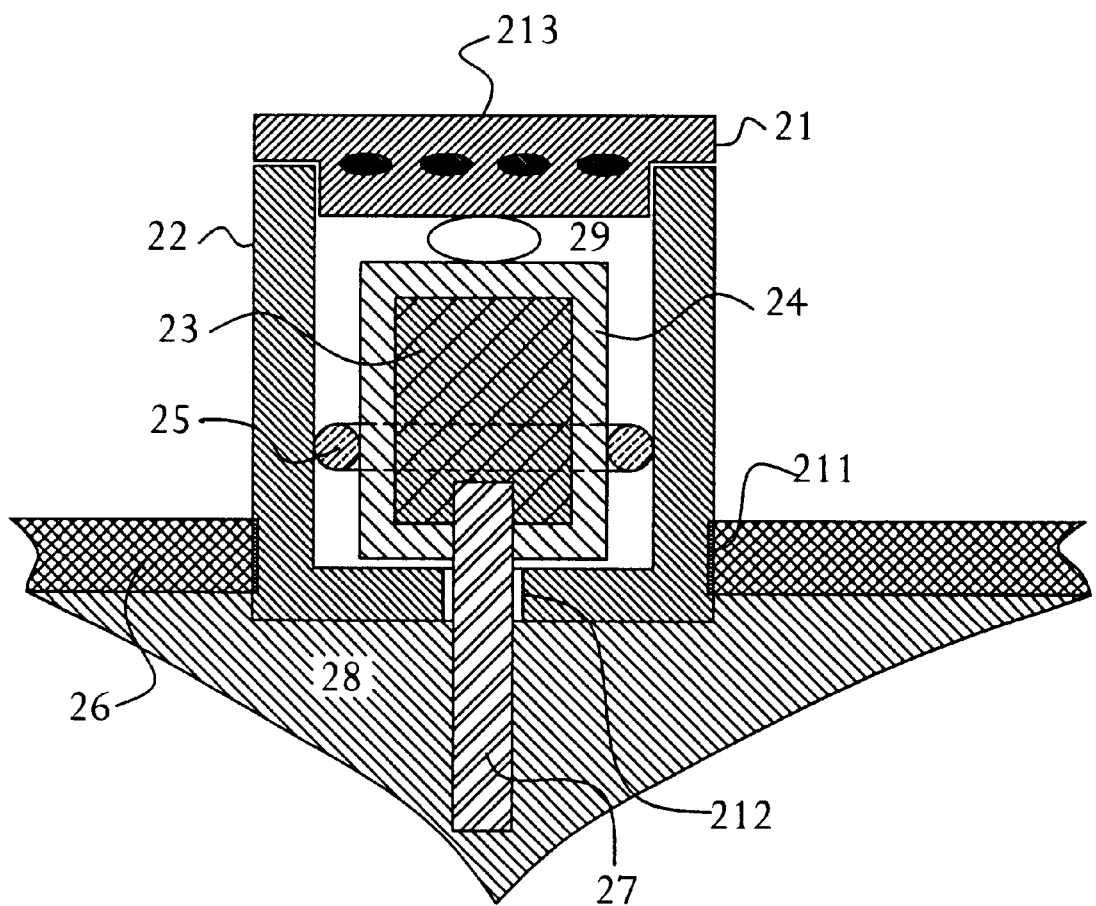
FIG. 7 is detail diagram of the half-cell in the lead battery of FIG. 6.

In FIG. 7, an example of the design is shown in more detail. A cylindrical plastic plug 22 with the thread 211 is inserted into the battery lid 26. A lead cup 24 is situated inside the plastic housing with the active negative lead mass 23 which contains the linear functional element 27 tightly enclosed. It extends into the active mass 23. A round constricting ring 25 enables the sliding back-and-forth motion of the cup 23 and that of the electrochemical key 27 firmly connected to it inside the electrolyte 28. The spring 29 forms the contact with the metal lid 21 and the outer connection 213. In the case of a plastic lid, connection 213 may also be a through-going contact screw or contact rivet.

Modifications of the construction of the subject of FIG. 7 are obvious; however, they should reflect the following state of affairs: the half-cell 3 of FIG. 6 at the second end of the electrochemical key 5 is an essentially closed hollow body of metallic lead or lead-plated metallic copper which contains a porous lead mass in the inner space and, in whose pore system, sulfuric acid is immobilized. The linear functional element opens in the inner space, penetrating the closed hollow body, as an electrochemical key. For the metallic hollow body, the condition is that the metal in question does not corrode at the potential of the negative lead electrode. In view of the fact that the metal hollow body is also in contact with the outside air, it should be corrosion-shielded there also. This can always be achieved by means of a stable plastic coating. Thus, referring again to FIG. 7, a shrink-fit hose can be used to seal both the functional element 27 in the cup 24 and also be used to perform the function of the plastic housing 22.

Figure 8:
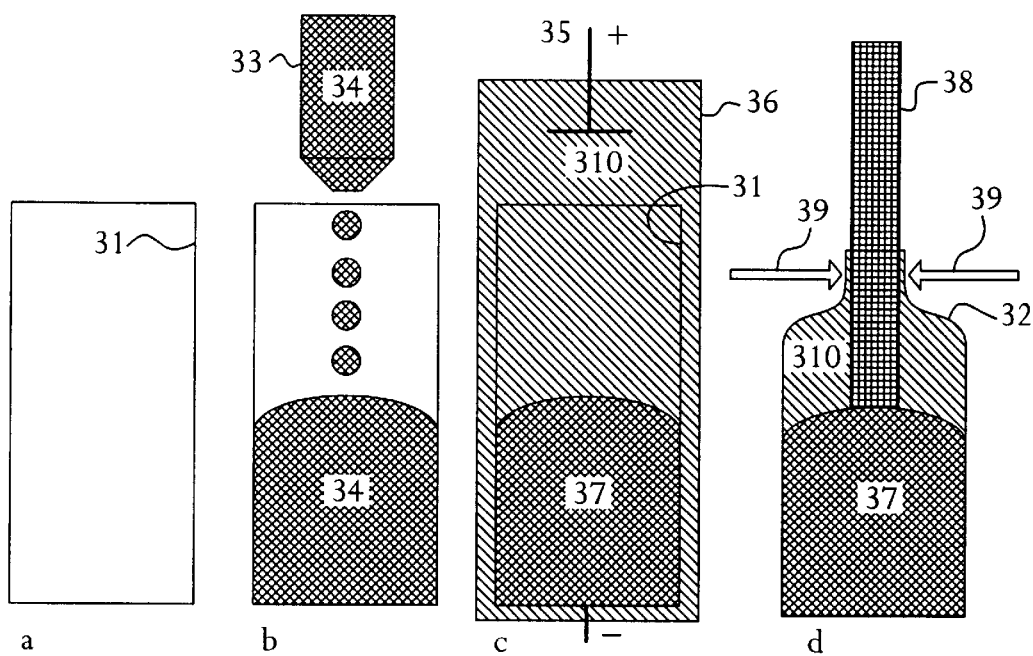
FIGS. 8a–d show a process for manufacturing the half-cell of FIG. 6.

It is important to be able to produce the structural elements of a charge state indicator in a simple way. One possibility for this is shown in FIG. 8, which shows the four phases (a), (b), (c), and (d) of an assembly line process. First, a lead cup 31 with a diameter of 0.5 to 1 cm and height of 0.5 to 2 cm is made by die-casting, injection molding, or deep drawing. The wall thickness should be as close to 0.1 cm as possible. For the choice of the alloy, the corrosion resistance is more important than the hardness. Therefore, whenever possible, pure lead will be used. The small cup is inserted into a conveyer belt or in a perforated plate as a holder. FIG. 8a shows the empty cup 31.

In the next station, FIG. 8b, the active mass is introduced as paste 34. It may consist of lead dust (oxidized lead with a high oxide content) and sulfuric acid. The paste is painted on or sprayed or injected from a nozzle 33. After a holding time under the preferred climatic conditions, the cup is inserted into the formation bath, FIG. 8c, of sulfuric acid. The container 36 of the formation bath may be formed from lead sheet and contain a large number of cups 31 with which it is in electronic contact. The counterelectrode 35 is guided through the formation trough in an insulated manner and immersed in the sulfuric acid 310 as the formation electrolyte. By the formation current, the paste 34 is transformed into lead sponge 37. After this production step, the cups are washed and provided with prepared sulfuric acid, optionally in the form of a gel. The linear functional element 38 is plugged in. Then, the cup is sealed with a gasket or, as indicated in FIG. 8d, pressed by the pressing plunger 39 without cutting, thus sealing it (32) around the element 38. A cylindrical linear element 38 is ideal for this, at least in this region.

On a lead cell equipped with the invention, such as that shown in FIG. 6, one can measure, at any operating time, two independent voltage values between the negative cell pole 1, the positive cell pole 2, and the half-cell 3, where $U_{1,2}$ is the voltage difference between the negative cell pole 1 and the positive cell pole 2, $U_{1,3}$ is the voltage difference between the negative cell pole 1 and the half-cell 3, and $U_{2,3}$ is the voltage difference between the positive cell pole 2 and the half-cell 3. For these voltages, the following signs are expected in the charging phase:

$$U_{1,2} > 0; \quad U_{1,3} > 0; \quad U_{2,3} < 0$$

In the final charging phase, accordingly:

$$U_{1,2} > 0; \quad U_{1,3} < 0; \quad U_{2,3} < 0$$

The voltage $U_{1,3}$ passes through the voltage value of zero between charging and discharging in the unloaded case if the electrolyte concentration in the negative electrode and in the half-cell agree. The nearly concordant electrode potential between the half-cell 3 and the negative 1 makes the voltage $U_{1,3}$ a sensitive indicator for the state of the cell. Upon charging, this voltage runs from positive values before the beginning of charging to the value of zero when the negative is fully charged. The beginning of hydrogen evolution then causes it to jump to a negative value $U_{1,3,gas}$. This event is the stimulus for the lowering of the charging current in order to bring the positive into the fully charged state later on. Now $U_{2,3}$ is the essential voltage which permits insight into the later processes of the battery. With the beginning of oxygen evolution on the positive, this voltage transitions to the value of $U_{2,3,gas}$ at which now the charging current stops or can be lowered to a small value for charge maintenance.

During discharging, the voltage $U_{1,3}$ in the current pauses indicates essentially the electrolyte concentration in the negative. To be sure, because of the necessary diffusion into the pore skeleton, the latter lies above that which would be adjusted after a longer waiting time. The ampere-hour counter indicates a deviant value. This circumstance can be utilized according to the idea disclosed above in German patent DE-PS 32 16 412 in order to calculate and indicate the immediate capacity standing available at any time.

By accepting certain disadvantages in the bargain, the linear functional element may consist of a highly porous material strip with strong wetting capacity by sulfuric acid whose capillary pressure in the interconnecting pores draws the liquid against the force of gravity to a height of at least 50 cm. This strip should be closely surrounded with an insulating jacket as a linear functional element.

It will be further understood that various changes in the details, materials, and arrangements of the parts which have been described and illustrated in order to explain the nature of this invention may be made by those skilled in the art without departing from the principle and scope of the invention as expressed in the following claims.

What is claimed is:

1. A linear electrochemical functional element, comprising a strip-shaped half-cell accessible at both ends and enclosed by a jacket of a solid insulating material.

2. The invention of claim 1, wherein the half-cell comprises a strip-shaped hydrogen-diffusion electrode.

3. The invention of claim 1, wherein the half-cell comprises a strip-shaped ion-exchange membrane (IEM).

4. The invention of claim 3, wherein the half-cell further comprises a strip-shaped hydrogen-diffusion electrode.

5. The invention of claim 1, wherein the jacket comprises a metal with a passivated surface.

6. The invention of claim 1, wherein the jacket comprises a synthetic resin.

7. The invention of claim 6, wherein the synthetic resin is a casting resin.

8. The invention of claim 1, wherein the half-cell is connected to a hydrogen source.

9. The invention of claim 1, wherein the functional element is part of a measuring electrode, wherein the half-cell is installed in a hydrogen tube of a hydrogen rod electrode with an integrated hydrogen source.

10. The invention of claim 1, wherein the functional element is part of a measuring electrode having two or more of the functional elements, wherein each half-cell is installed in a hydrogen tube of a hydrogen rod electrode with an integrated hydrogen source.

11. The invention of claim 1, wherein:

the half-cell comprises a strip-shaped ion-exchange membrane (IEM) and a strip-shaped hydrogen-diffusion electrode;

the jacket comprises a synthetic resin or a metal with a passivated surface the functional element is part of a measuring electrode, wherein the half-cell is installed in a hydrogen tube of a hydrogen rod electrode with an integrated hydrogen source.

12. The invention of claim 11, wherein the functional element is part of a measuring electrode having two or more of the functional elements, wherein each half-cell is installed in a hydrogen tube of a hydrogen rod electrode with an integrated hydrogen source.

13. The invention of claim 12, wherein the measuring electrode further comprises an additional half cell that is open to access of oxygen from air to form a fuel cell that allows to control proper function of the hydrogen supply and of the hydrogen electrodes.

* * * * *